United States Patent
Merkle et al.

(10) Patent No.: US 6,229,022 B1
(45) Date of Patent: May 8, 2001

(54) METHOD FOR PRODUCING SUBSTITUTED PYRAZOLES

(75) Inventors: Hans Rupert Merkle, Ludwigshafen; Erich Fretschner, Neckarsteinach, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/445,766

(22) PCT Filed: Jun. 22, 1998

(86) PCT No.: PCT/EP98/03814

§ 371 Date: Dec. 13, 1999

§ 102(e) Date: Dec. 13, 1999

(87) PCT Pub. No.: WO98/58914

PCT Pub. Date: Dec. 30, 1998

(30) Foreign Application Priority Data

Jun. 23, 1997 (DE) ............................................. 197 26 573

(51) Int. Cl.⁷ ................................................. C07D 231/10
(52) U.S. Cl. ............................................................ 548/373.1
(58) Field of Search .............................. 548/373.1, 376.1, 548/377.1

(56) References Cited

U.S. PATENT DOCUMENTS

| 4,423,225 | | 12/1983 | Lantzsch et al. | ..................... 548/373 |
| 4,424,364 | | 1/1984 | Goetz et al. | ......................... 548/373 |
| 4,434,292 | | 2/1984 | Heinemann et al. | ................. 548/373 |
| 5,569,769 | * | 10/1996 | Merkle et al. | ..................... 548/373.1 |

FOREIGN PATENT DOCUMENTS

| 3209148 | 9/1983 | (DE) . |
| 3415385 | 10/1985 | (DE) . |
| 402722 | 12/1990 | (EP) . |
| 474037 | 3/1992 | (EP) . |
| 95/06036 | 3/1995 | (WO) . |

* cited by examiner

Primary Examiner—Joseph K. McKane
Assistant Examiner—Joseph Murray
(74) Attorney, Agent, or Firm—Keil & Weinkauf

(57) ABSTRACT

Pyrazole derivatives are prepared by reacting carbonyl compounds $R^1$—C(O)—CH($R^2$)—CH$_2R^3$ with hydrazine, its hydrate or its salts in 30 to 100% by weight sulfuric acid in the presence of catalytic amounts of iodine or of an iodine compound.

7 Claims, No Drawings

METHOD FOR PRODUCING SUBSTITUTED PYRAZOLES

The present invention relates to a process for preparing pyrazole derivatives.

Numerous ways of synthesizing pyrazole are described in "The Chemistry of Heterocyclic Compounds", Volume 22, Chapters 3 and 5, for example condensation of α,β-dicarbonyl compounds with hydrazines, reaction of ethynyl-carbonyl compound with hydrazines and condensation of hydrazinoacetic ester with 1,2-diketones.

It is furthermore known to dehydrogenate 2-pyrazoline with chlorine, alkali metal or alkaline earth metal hypochlorites (DE-A 30 35 395), with sulfur or selenium (DE-A 30 29 160) or with aqueous hydrogen peroxide (DE-A 34 15 385) to give pyrazole. Also known are the thermal gas-phase dehydrogenation of 2-pyrazoline on palladium or platinum catalysts (DE-A 32 09 148) and the thermolysis of N-sulfonyl-2-pyrazoline to pyrazole (DE-A 30 35 394).

In addition, the dehydrogenation of 2-pyrazolines in sulfuric acid in the presence of iodine compounds has been described. In EP 0 474 037, the pyrazoline is generated in situ from an unsubstituted or substituted hydrazine and 2-butene-1,4-diol, 1-butene-3,4-diol or ethynylalkylcarbinol. In WO 95/06036, the pyrazoline is first prepared from an unsubstituted or substituted hydrazine and an α,β-unsaturated carbonyl compound and is then, after mixing with sulfuric acid and the iodine catalyst, dehydrogenated. In EP 0 402 722, the pyrazoline is prepared beforehand or in situ from an unsubstituted or substituted hydrazine and a glycerol, an acrolein or vinyl alkyl ketone or a β-hydroxyethyl alkyl ketone.

However, these processes are industrially unsatisfactory, whether because they require the use of very aggressive oxidizing agents or costly catalysts, are associated with the formation of toxic by-products such as hydrogen sulfide and selenide, the compounds employed can be obtained only with difficulty, or they comprise a plurality of steps.

It is an object of the present invention to provide a process for preparing pyrazole derivatives which can be carried out industrially more simply and more economically.

We have found that this object is achieved by a process for preparing pyrazole derivatives of the formula I

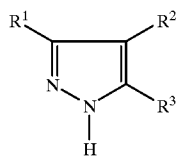

(I)

where $R^1$, $R^2$ and $R^3$ are, independently of one another, a hydrogen atom or an unsubstituted or substituted alkyl, cycloalkyl, aryl or aralkyl group, which comprises reacting a carbonyl compound of the formula II

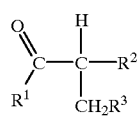

(II)

where $R^1$, $R^2$ and $R^3$ have the abovementioned meanings, with hydrazine, hydrazine hydrate or an acid addition salt thereof, in the presence of sulfuric acid and iodine or of a compound which liberates iodine or hydrogen iodide.

Carbonyl compounds of the formula II suitable for the novel process are those where $R^1$, $R^2$ and $R^3$ are, independently of one another, selected from a hydrogen atom, a straight-chain or branched alkyl, such as $C_1$–$C_8$-alkyl, in particular $C_1$–$C_4$-alkyl, such as methyl, ethyl, propyl, 1-methylethyl, butyl, 1-methylpropyl, 2-methylpropyl and 1,1-dimethylethyl; $C_3$–$C_8$-cycloalkyl such as, in particular, cyclopentyl, cyclohexyl and cycloheptyl; $C_6$–$C_{14}$-aryl such as, in particular, phenyl; aralkyl such as, in particular, phenyl-$C_1$–$C_4$-alkyl, where the alkyl radical is as defined above, eg. benzyl and 2-phenylethyl; and corresponding organic radicals substituted by one or more halogen atoms such as F, Cl, Br or I, nitro, sulfo or sulfonyl groups, such as, in particular, chlorophenyl, nitrophenyl or tolyl.

Carbonyl compounds of the formula II preferred in the novel process are those where $R^2 \neq$ hydrogen. $R^2$ is, in particular, methyl. $R^3$ is preferably hydrogen. It is particularly preferred for $R^2$ to be methyl and $R^3$ to be hydrogen. It is furthermore preferred for $R^1$ in compounds of the formula II to be hydrogen, methyl, ethyl, n-propyl, tert-butyl, phenyl, o-, m- or p-tolyl, o-, m- or p-chlorophenyl, o-, m- or p-nitrophenyl, o-, m- or p-sulfophenyl, or o-, m- or p-sulfonylphenyl.

Particularly suitable carbonyl compounds are the following: isobutyraldehyde, methyl isopropyl ketone (2-methyl-3-butanone), ethyl isopropyl ketone (2-methyl-3-pentanone), n-propyl isopropyl ketone (2-methyl-3-hexanone), isopropyl t-butyl ketone, phenyl isopropyl ketone, tolyl isopropyl ketone, chlorophenyl isopropyl ketone, nitrophenyl isopropyl ketone, sulfonylphenyl isopropyl ketone and sulfophenyl isopropyl ketone.

Hydrazine is used as second reaction component. It is possible to employ both the free hydrazine base and its hydrates or addition salts with mineral acids, eg. the salts of hydrazine with sulfuric acid, hydrochloric acid or phosphoric acid. Since losses of yield may occur on use of salts which do not dissolve in the reaction medium, it is preferred to use the hydrate or the free base.

Sulfuric acid is used in the novel process as diluent, condensing agent and oxidizing agent. Its concentration is preferably in the range from 30 to 100% by weight, in particular in the range from 45 to 90% by weight.

It is possible, where appropriate, to employ inert organic solvents such as chlorinated hydrocarbons, eg. dichloroethane, as additional diluent.

It is possible to use as catalyst besides elemental iodine also iodine compounds such as hydrogen iodide, alkali metal and alkaline earth metal iodides such as lithium iodide, sodium iodide, potassium iodide, cesium iodide, magnesium iodide and calcium iodide, and other metal iodides. It is also possible to use other inorganic iodine compounds such as alkali metal or alkaline earth metal hypoiodites, iodites, iodates and periodates, or organic iodine compounds such as alkyl iodides, eg. methyl iodide. Iodine or the iodine compound is generally employed in this reaction in amounts of from 0.01 to 10 mol-%, in particular from 0.05 to 5 mol-%, based on hydrazine.

When hydrazine hydrate and methyl isopropyl ketone are used with hydrogen iodide as catalyst, the reaction can be represented by the following equations:

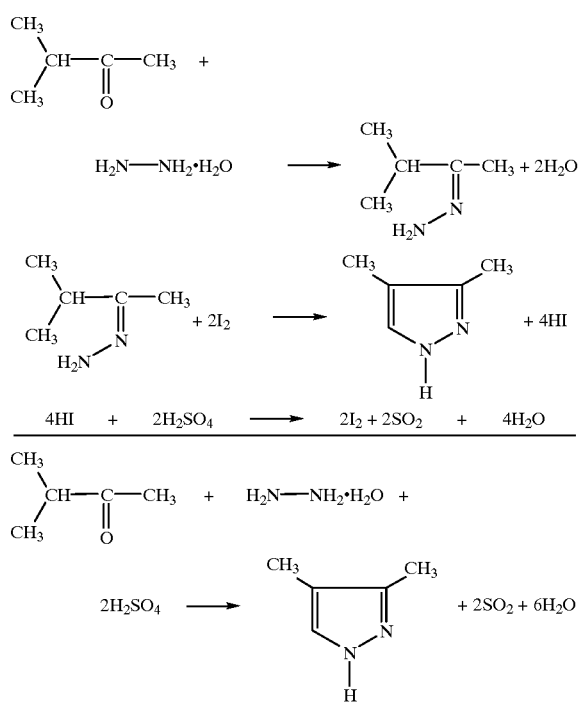

On use of isobutyraldehyde as carbonyl compound, hydrazine hydrate and hydrogen iodide as catalyst, the process reactions can be represented by the following equations:

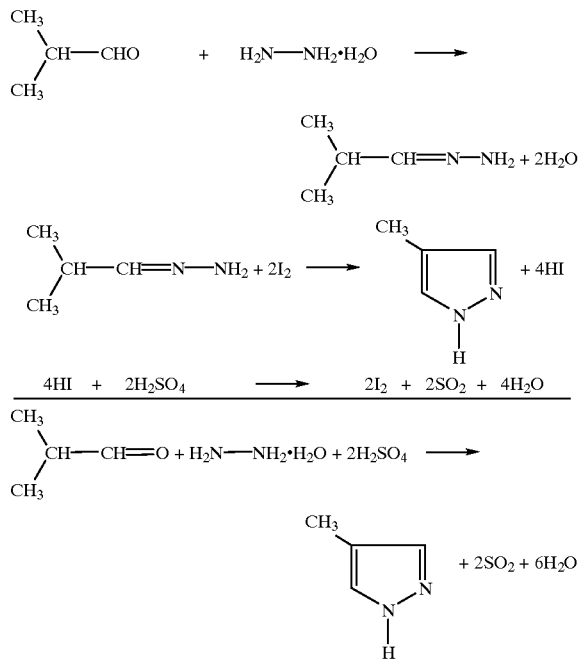

The reaction is expediently carried out by reacting 1 mol of the hydrazine compound with from 0.5 to 2, preferably 0.8 to 1.5, mol of the carbonyl compound of the formula II in sulfuric acid in the presence of catalytic amounts of an iodine compound, it being possible to remove the water which is present in the reaction mixture and is formed additionally. This removal preferably takes place by distillation, for example under atmospheric pressure. The reaction temperatures are in the range from 50 to 250° C., preferably from 80 to 200° C. and, in particular, from 110 to 170° C. The reaction is normally carried out under atmospheric pressure. It is also possible to carry out the reaction under elevated pressure or, with appropriately raised temperature, in less concentrated sulfuric acid or under reduced pressure or, with appropriately reduced temperature, in more concentrated sulfuric acid.

The reaction can be carried out by all the reactants being placed in a vessel and brought to the reaction temperature, by feeding the reactants as mixture or separately from one another into a vessel at the reaction temperature, or by introducing part of the reactants at the reaction temperature and feeding the remaining quantity in during the reaction. It is also possible for the sulfuric acid itself or hydrazine/sulfuric acid to be initially present in the reaction vessel.

The reaction temperature is preferably reached by distilling water out. The onset of pyrazole formation is evident from the evolution of sulfur dioxide. Absorption of the sulfur dioxide with sodium hydroxide solution affords equimolar amounts of sodium bisulfite solution of high purity. The water which is distilled off contains most of the iodide employed in the form of hydrogen iodide, which can be recycled.

The reaction mixture is worked up to isolate the pyrazole by conventional processes. The dark brown reaction mixture is preferably worked up by neutralization, eg. with sodium hydroxide solution, ammonia or other inorganic bases. To isolate the pyrazole, the neutralized reaction mixture is, for example, extracted several times with a solvent. Examples of suitable solvents are isobutanol, chlorinated hydrocarbons or tetrahydrofuran. Drying of the extraction solution and evaporation to dryness result in the corresponding pyrazoles with a purity of from 80 to 90%. These crude products can be distilled or recrystallized to improve the purity. The neutralized reaction mixture can also be worked up by distillation, in which case water and pure pyrazole are distilled out, and sodium sulfate (or ammonium sulfate) contaminated with organic by-products remains as residue. On neutralization with ammonia, the bottom product from the distillation is impure ammonium sulfate which can be oxidized to nitrogen and sulfur dioxide. The latter can be converted back, through $SO_3$, into sulfuric acid.

The process can be carried out continuously or batchwise and under atmospheric, elevated or slightly reduced pressure.

The pyrazole compounds of the formula I which can be prepared by the novel process are starting materials for organic syntheses, eg. for pharmaceutical products and crop protection agents. The following compounds are particularly preferably prepared by the novel process: 4-methylpyrazole, 3,4-dimethylpyrazole, 3-ethyl-4-methylpyrazole, 3-n-propyl-4-methylpyrazole, 3-t-butyl-4-methylpyrazole, 3-phenyl-4-methylpyrazole, 3-tolyl-4-methylpyrazole, 3-chlorophenyl-4-methylpyrazole and 3-nitrophenyl-4-methylpyrazole.

The following examples serve to illustrate the novel process.

EXAMPLES

Example 1

Preparation of 3,4-Dimethylpyrazole
(Compound of the Formula I where $R^1$ is Methyl, $R^2$ is Methyl and $R^3$ is H)

111.8 g (1.3 mol) of 3-methyl-2-butanone are added dropwise over the course of 3 hours to a suspension of 560 g (4.0 mol) of 70% strength sulfuric acid, 62.5 g (1.0 mol)

of 80% strength hydrazine hydrate and 1 g (6.67 mmol) of sodium iodide, starting at 120° C. The temperature falls to 110° C. during the addition. After the addition is complete, the temperature is brought to 130° C. by distilling out 210 ml of water over the course of 2 hours, and the mixture is stirred at this temperature for 30 minutes. The 210 ml of water distilled off are added at 100° C. and then the mixture is cooled and adjusted to pH 9 with 655 g (4.1 mol) of 25% strength sodium hydroxide solution. After extraction with isobutanol, the organic phase is concentrated and then distilled under reduced pressure.

79.9 g of 3,4-dimethylpyrazole with a purity of 99.2% are obtained. This corresponds to a yield of 82.6% of theory; boiling point: 90° C. (under 5 mbar). Identification took place through the physicochemical data.

Example 2
Preparation of 3-Phenyl-4-Methylpyrazole
(Compound of the Formula I where $R^1$ is Phenyl, $R^2$ is Methyl, $R^3$ is H)

74.8 g (0.505 mol) of isopropyl phenyl ketone are added dropwise over the course of 2 hours to a suspension of 490 g (3.0 mol) of 60% strength sulfuric acid, 31.25 g (0.5 mol) of 80% strength hydrazine hydrate and 0.5 g (3.33 mmol) of sodium iodide at 125° C. After stirring at 125° C. for one hour, the temperature is brought to 140° C. by distilling out 155 ml of water. After cooling, the mixture is adjusted to pH 7.5 with 640 g (4.0 mol) of sodium hydroxide solution. The residue after filtration and drying was recrystallized from ethanol.

69.2 g of pale brown crystals are obtained with a melting point of 115° C. and a purity of 97% (HPLC), which corresponds to a yield of 85% of theory. Identification takes place through the physicochemical data.

Example 3
Preparation of 4-Methylpyrazole
(Compound of the Formula I where $R^1$ is H, $R^2$ is Methyl, $R^3$ is H)

1.0 g (6.67 mmol) of sodium iodide is added to a suspension of 560 g (4.0 mol) of 70% strength sulfuric acid and 62.5 g (1.0 mol) of 80% strength hydrazine hydrate and, at 125° C., 86.4 g (1.2 mol) of isobutyraldehyde are pumped under the surface of the suspension over the course of 2 hours using a metering pump. During and up to 100 minutes after the addition of isobutyraldehyde, a total of 175 g of water was distilled out, with the temperature of the mixture rising to 135° C. toward the end. The solution is cooled and adjusted to pH 8.6 with 820 g (5.125 mol) of 25% strength sodium hydroxide solution and is extracted with isobutanol. The combined extracts are concentrated to 82 g in a rotary evaporator and then distilled.

The main fraction (boiling point 82° C. under 7 mbar; 49 g) consists of 82% 4-methylpyrazole which was identified by comparison with authentic material. Yield: 49% of theory.

Example 4
Preparation of 3-Ethyl-4-Methylpyrazole
(Compound of the Formula I where $R^1$ is Ethyl, $R^2$ is Methyl, $R^3$ is H)

27.5 g (0.275 mol) of 2-methyl-3-pentanone are added dropwise to a suspension of 280 g (2.0 mol) of 70% strength sulfuric acid, 12.5 g (0.25 mol) of 100% hydrazine hydrate and 0.5 g (3.33 mmol) of sodium iodide at 125° C. After the addition is complete, the temperature is brought to 110° C. over the course of 1 hour and stirring is continued at this temperature for 6 hours. The reaction mixture is cooled and adjusted to pH 9 with 480 g (3.0 mol) of 25% strength sodium hydroxide solution. After extraction with isobutanol, the organic phase is concentrated and then distilled under reduced pressure.

18.5 g of 3-ethyl-4-methylpyrazole are obtained with a boiling point of 90° C. under 5 mbar and a purity of 95% (HPLC), which corresponds to a yield of 63.9% of theory. Identification takes place by comparing the physicochemical data with an authentic sample.

We claim:

1. A process for preparing pyrazole derivatives of the formula I

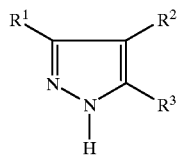

where $R^1$ and $R^2$ are, independently of one another, an unsubstituted or substituted $C_1$–$C_8$-alkyl, $C_3$–$C_8$-cycloalkyl, $C_6$–$C_{14}$-aryl or phenyl-$C_1$–$C_4$-alkyl group, $R^1$ can also be hydrogen, and $R^3$ is hydrogen which comprises reacting a carbonyl compound of the formula II

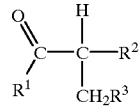

where $R^1$, $R^2$ and $R^3$ have the abovementioned meanings, with hydrazine, hydrazine hydrate or an acid addition salt thereof, in the presence of a 30 to 100% per weight sulfuric acid and from 0.05 to 5 mol %, based on the hydrazine compound, of iodine or of a compound which liberates iodine or hydrogen iodide at from 80 to 200° C. wherein hydrazine compound and carbonyl compound are employed in a molar ratio of from 1:0.8 to 1:1.5.

2. A process as claimed in claim 1, wherein the sulfuric acid used is from 45 to 90% by weight.

3. A process as claimed in claim 1, wherein the reaction is carried out at from 110 to 170° C.

4. A process as claimed in claim 1, wherein the reaction is carried out under atmospheric pressure.

5. A process as claimed in claim 1, wherein water produced in the reaction is removed from the reaction mixture.

6. A process as claimed in claim 1, wherein a carbonyl compound of the formula II where $R^1$ has the stated meanings, $R^2$ is methyl and $R^3$ is a hydrogen atom is employed.

7. A process as claimed in claim 1, wherein a compound where $R^1$ is a hydrogen atom, methyl, ethyl, n-propyl, t-butyl, phenyl, tolyl, chlorophenyl, sulfophenyl, sulfonylphenyl or nitrophenyl, $R^2$ is methyl and $R^3$ is a hydrogen atom is obtained.

* * * * *